US009359585B2

(12) United States Patent
Spadini et al.

(10) Patent No.: US 9,359,585 B2
(45) Date of Patent: *Jun. 7, 2016

(54) STABLE NONAQUEOUS REACTIVE SKIN CARE AND CLEANSING COMPOSITIONS HAVING A CONTINUOUS AND A DISCONTINUOUS PHASE

(75) Inventors: Alessandro Luigi Spadini, Stamford, CT (US); Melissa Iva Katz, Weston, CT (US); David Robert Williams, Monroe, CT (US); Marcina Siciliano, New Haven, CT (US); Evan Hillman, Torrington, CT (US); Andre Puleo, Bethany, CT (US); Megan Kathleen Hurley, Middletown, CT (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 1959 days.

This patent is subject to a terminal disclaimer.

(21) Appl. No.: 10/730,218

(22) Filed: Dec. 8, 2003

(65) Prior Publication Data

US 2005/0123573 A1 Jun. 9, 2005

(51) Int. Cl.
*A61K 8/04* (2006.01)
*A61K 8/22* (2006.01)
*A61K 8/26* (2006.01)
*A61K 8/36* (2006.01)
*A61K 8/365* (2006.01)
*A61K 8/46* (2006.01)
*A61Q 9/04* (2006.01)
*A61Q 19/10* (2006.01)
*C11D 10/04* (2006.01)
*C11D 17/00* (2006.01)
*A61Q 5/08* (2006.01)

(52) U.S. Cl.
CPC .............. *C11D 17/006* (2013.01); *A61K 8/22* (2013.01); *A61K 8/46* (2013.01); *A61Q 5/08* (2013.01); *A61Q 9/04* (2013.01); *A61Q 19/10* (2013.01); *C11D 17/0004* (2013.01); *A61K 2800/222* (2013.01); *A61K 2800/42* (2013.01)

(58) Field of Classification Search
None
See application file for complete search history.

(56) References Cited

U.S. PATENT DOCUMENTS

| 1,682,119 | A | | 8/1928 | Field |
|---|---|---|---|---|
| 2,607,940 | A | | 8/1952 | Miller |
| 3,167,805 | A | | 2/1965 | Zuppinger et al. |
| 3,194,736 | A | | 7/1965 | Braun et al. |
| 3,850,831 | A | | 11/1974 | Hellsten et al. |
| 3,866,800 | A | | 2/1975 | Schmitt et al. |
| 4,190,550 | A | | 2/1980 | Campbell |
| 4,228,834 | A | | 10/1980 | Desnick |
| 4,372,867 | A | | 2/1983 | Taragos |
| 4,480,939 | A | | 11/1984 | Upton |
| 4,678,704 | A | | 7/1987 | Fellows |
| 4,704,271 | A | * | 11/1987 | Hourihan et al. ............... 424/66 |
| 4,722,836 | A | * | 2/1988 | Geary et al. .................... 424/68 |
| 4,789,262 | A | | 12/1988 | Sanchez |
| 4,828,723 | A | * | 5/1989 | Cao et al. ...................... 510/304 |
| 4,837,008 | A | | 6/1989 | Rudy et al. |
| 4,888,323 | A | * | 12/1989 | Matsuda et al. ................ 512/23 |
| 4,923,478 | A | * | 5/1990 | Naggiar ............................ 8/161 |
| 4,929,644 | A | | 5/1990 | Guilbeaux |
| 4,987,632 | A | | 1/1991 | Rowe |
| 5,020,694 | A | | 6/1991 | Pettengill |
| 5,147,576 | A | | 9/1992 | Montague |
| 5,316,054 | A | | 5/1994 | Hall et al. |
| 5,434,069 | A | * | 7/1995 | Tsaur .................. C11D 3/38672 252/79.1 |
| 5,462,378 | A | | 10/1995 | Webb |
| 5,466,390 | A | * | 11/1995 | Houghton et al. ............ 510/407 |
| 5,508,394 | A | * | 4/1996 | Kappes et al. ............... 536/55.2 |
| 5,585,093 | A | | 12/1996 | Murphy |
| 5,612,307 | A | * | 3/1997 | Chambers et al. ............ 510/406 |
| 5,720,949 | A | | 2/1998 | Davis |
| 5,839,842 | A | | 11/1998 | Wanat et al. |
| 5,876,758 | A | * | 3/1999 | Meybeck et al. ............. 424/490 |
| 5,918,590 | A | * | 7/1999 | Burkett ................... A61F 7/034 126/204 |
| 5,939,082 | A | * | 8/1999 | Oblong et al. ................ 424/401 |
| 5,952,286 | A | * | 9/1999 | Puvvada et al. .............. 510/417 |
| 5,958,454 | A | | 9/1999 | Schrempf |
| 5,997,887 | A | * | 12/1999 | Ha et al. ....................... 424/401 |

(Continued)

FOREIGN PATENT DOCUMENTS

EP 0 266 124 5/1988
EP 0319168 A1 * 6/1989 .............. A61K 8/26

(Continued)

OTHER PUBLICATIONS

Webster's New Collegiate Dictionary.1981, p. 162, and p. 1153.*

(Continued)

*Primary Examiner* — Bethany Barham
*Assistant Examiner* — Lisbeth C Robinson
(74) *Attorney, Agent, or Firm* — Ronald A. Koatz

(57) ABSTRACT

In one embodiment, a liquid or flowable cleansing or skin treatment composition is described which is substantially nonaqueous and which has a continuous and a discontinuous phase. Components of the discontinuous phase can chemically react with each other or with water when water is blended with the nonaqueous cleansing or skin treatment composition during consumer use. In a second embodiment, a solidified cleansing or skin treatment composition is described which contains components that can chemically react with each other or with water when water is blended with the solidified cleansing composition during consumer use. Methods for treating the skin with the inventive compositions are also described.

10 Claims, No Drawings

(56) References Cited

U.S. PATENT DOCUMENTS

| | | | |
|---|---|---|---|
| 6,042,288 A | 3/2000 | Rattinger et al. | |
| 6,063,390 A * | 5/2000 | Farrell et al. | 424/404 |
| 6,161,729 A | 12/2000 | Gentile et al. | |
| 6,174,533 B1 * | 1/2001 | SaNogueira et al. | 424/401 |
| 6,177,092 B1 | 1/2001 | Lentini et al. | |
| 6,183,766 B1 | 2/2001 | Sine et al. | |
| 6,248,363 B1 * | 6/2001 | Patel et al. | 424/497 |
| 6,274,127 B1 | 8/2001 | Schraer et al. | |
| 6,287,580 B1 * | 9/2001 | Gott | A61K 8/02 424/400 |
| 6,290,943 B1 | 9/2001 | Naser et al. | |
| 6,294,186 B1 * | 9/2001 | Beerse et al. | 424/405 |
| 6,310,014 B1 | 10/2001 | Rau | |
| 6,403,065 B1 * | 6/2002 | Chevalier et al. | 424/62 |
| 6,416,768 B1 * | 7/2002 | Ravaux et al. | 424/401 |
| 6,451,327 B1 | 9/2002 | Nakagaki et al. | |
| 6,492,326 B1 * | 12/2002 | Robinson et al. | 514/2 |
| 6,569,415 B1 | 5/2003 | Orloff et al. | |
| 6,607,733 B1 * | 8/2003 | Diec et al. | 424/401 |
| 6,630,438 B1 | 10/2003 | Arnau | |
| 6,780,826 B2 * | 8/2004 | Zhang et al. | 510/130 |
| 2002/0192173 A1 | 12/2002 | Glenn et al. | |
| 2002/0193256 A1 | 12/2002 | Harris et al. | |
| 2003/0003064 A1 * | 1/2003 | Kalla | A61K 8/11 424/63 |
| 2003/0103920 A1 * | 6/2003 | Clare et al. | 424/65 |
| 2003/0108506 A1 | 6/2003 | Scholz et al. | |
| 2004/0062735 A1 * | 4/2004 | Sun et al. | 424/70.1 |
| 2005/0042262 A1 | 2/2005 | Hasenoehrl et al. | |

FOREIGN PATENT DOCUMENTS

| | | |
|---|---|---|
| EP | 0 897 719 | 2/1999 |
| GB | 2 242 358 | 10/1991 |
| GB | 2 386 604 | 9/2003 |
| JP | 10137152 | 5/1998 |
| WO | 97/40814 | 11/1997 |
| WO | 97/45525 | 12/1997 |
| WO | 99/24546 | 5/1999 |
| WO | 01/08657 | 2/2001 |
| WO | 02/02730 | 1/2002 |
| WO | 02/069917 A2 | 9/2002 |
| WO | 02/069917 A3 | 9/2002 |
| WO | 03/070211 | 8/2003 |
| WO | 2004/058214 | 7/2004 |

OTHER PUBLICATIONS

Steadman's Medical Dictionary. 1995; p. 1259.*
Optigel SH Synthetic Siliate, ChemBrief. Jun. 2003, vol. 3, Issue 2.*
Condensed Chemical Dictionary, 1971, Van Nostrane Reinhold Co., (8th ed. by Gessner Hawley), p. 674, "Phase" (2).*
Nibu et al. Journal of Colloid and Interface Science, 205: 305-315 (1998).*
Bentone-38. Elementis MSDS (2008) accessed at http://www.elementis.com/esweb/webproducts.nsf/allbydocid/2D26F5867C3CE10D852575F2005B119D/$FILE/BENTONE%2038%20Grease%20DS.pdf, on Oct. 23, 2013.*
Rheox acquisition. icis.com (1998) accessed at http://www.icis.com/Articles/1998/02/02/52682/elementis-completes-rheox-acquisition.html on Oct. 23, 2013.*
NTP Methylcellulose, National Toxicology Program, accessed at http://ntp.niehs.nih.gov/?objectid=E8841149-BDB5-82F8-F391629C17BE9A8B on Oct. 23, 2013.*
Courtney et al., Medical Device & Diagnostic Industry Magazine (1999) pp. 1-9, downloaded from http://www.mddionline.com/article/advances-cyanoacrylate-technology-device-assembly on May 29, 2014.*
Applicant: Spadini, et al. U.S. Appl. No. 10/730,709, filed Dec. 8, 2003 For: Stable Liquid Reactive Skin Care and Cleansing Packaged Product.
Applicant: Spadini, et al. U.S. Appl. No. 10/742,984, filed Dec. 22, 2003 For: Personal Care Implement Containing a Stable Reactive Skin Care and Cleansing Composition.
Lefers et al., Amphipathic definition, Amphipathic definition, 2004, p. 1.
Co-pending Application Spadini, et al. U.S. Appl. No. 12/893,096, filed Sep. 29, 2010 (issued as U.S. Pat. No. 8,357,383 B2).
Co-pending Application Spadini, et al. U.S. Appl. No. 13/714,811, filed Dec. 14, 2012.

* cited by examiner

STABLE NONAQUEOUS REACTIVE SKIN CARE AND CLEANSING COMPOSITIONS HAVING A CONTINUOUS AND A DISCONTINUOUS PHASE

BACKGROUND

1. Field of the Invention

The present invention relates to liquid or solidified skin care or cleansing compositions.

2. Background of the Invention

Conventional aqueous based liquid cleansing products have been traditionally used by consumers for personal cleansing. Frequently such products have compositions that are diluted with water to pre-solubilize or disperse the surfactant and benefit agent ingredients and are purchased by consumers in their diluted state. Consumers desiring to purchase a product containing a concentrated liquid version of such a cleansing composition, with reduced levels of water, are frequently faced with a very viscous and inconvenient to use product. Consumers also desire to purchase skin care and cleansing compositions with active ingredients that are freshly prepared and have a high degree of activity for its intended function. Concentrated nonaqueous cleansing products and compositions are known, some of which having active ingredients that are activated during use. For example, PCT publication no. WO 02/069917 to Glenn et al. published on Sep. 12, 2002 discloses an oil-in-oil emulsion that contains cosmetic actives that react with amino acid substrates where an internal oil solvates the reactive agent. U.S. publication No. 2002/0192173 to Glenn et al. published on Dec. 19, 2002 discloses an anhydrous treatment composition comprising an agent that reacts with amino acid based substrates and a solvent which solvates the reactive agent and which is water miscible. U.S. Pat. No. 6,451,327 issued to Masaaki et al. on Sep. 17, 2002 discloses a substantially nonaqueous, water-miscible skin cleansing composition containing a granulated surfactant. U.S. Pat. No. 6,569,415 issued to Orloff et al. on May 27, 2003 discloses an indicating shaving preparation product that undergoes a discernible physical or chemical change after a sufficient amount of water has been intermixed with the shaving preparation. Physical or chemical changes are described to take place in the shaving preparation itself or by disrupting encapsulated active ingredients dispersed within the shaving preparation and allowing the active ingredients to react with water or other components of the preparation. Also described by Orloff et al. is one embodiment of the product dispenser that contains two chambers that are isolated from each other and a system for blending the components together to allow them to react upon dispensing. There is no disclosure or suggestion however of unsolvated dispersed phase active ingredients that are not encapsulated in a barrier material prior to activation. Another example of a nonaqueous reactive product is provided in U.S. Pat. No. 6,274,127 issued to Schraer et al. on Aug. 14, 2001 which discloses an antiperspirant composition containing water reactive monomers in a nonaqueous base that polymerize when activated by the moisture in perspiration. A further example of a solid nonaqueous reactive product is provided in U.S. Pat. No. 3,194,736 issued to Braun on Jul. 13, 1965 which discloses a solid depilatory composition containing a dispersed sulfide ion precursor and an alkali in a waxy base that is activated by moisture applied to the skin.

Surprisingly it has been found that a skin care or cleansing composition can be formulated which has a substantially solvated or continuous and a substantially unsolvated or discontinuous phase where at least two components of the discontinuous phase may either react with each other when blended with water or where at least one component may itself react with the water so as to provide a unique cleansing, skin benefit, sensory signal or a combination thereof to the user. Such a composition also solves the problem of providing a concentrated cleansing or skin benefit component in a convenient liquid or solid form for consumer use.

SUMMARY OF THE INVENTION

In one aspect of the invention is a skin care or cleansing composition, including but not limited to:

a. a dispersed phase composed of a first component, the first component being capable of chemically reacting with a second component that is different from the first component b. a continuous phase present in the composition composed of a substantially anhydrous carrier;

c. at least one stabilizer contained in the dispersed phase wherein the stabilizer is selected from an organophilic particle, an amphipathic compound or polymer, or a crystalline hydroxyl containing stabilizer;

d. wherein the first component is substantially unsolvated in the carrier (preferably where the reactive component's solubility in the carrier is less than about 5, 3, 2, 1, 0.5, or 0.1% by wt. at 25° C.); and e. an anionic surfactant in a concentration of at least 2, 3, 5, 7, 9, 10, 15, 20, or 30% by wt. when the at least one stabilizer consists solely of waxy particles, amphipathic compounds or polymers, or a combination thereof.

Chemically reacting as used herein is defined as but is not limited to gas formation, redox reactions, lysis (e.g. hydrolysis and perhydrolysis), bond cleavage and the like; and does not include reactions or interactions that manifest themselves solely by one or more of the following: 1) color formation or color change, 2) self-polymerization and 3) exothermic or endothermic solvation processes. Chemical reactions are not excluded from the invention merely because they are accompanied by color change, self-polymerization, and exothermic or endothermic salvation processes if they also include at least one other definable chemical reaction. Preferably the first and second components are not encapsulated in a barrier material prior to reaction or at any time.

Substantially anhydrous as used herein means that the carrier is sufficiently free of water to prevent substantial solvation or reaction with the first component. Substantially anhydrous as used herein can also mean that the carrier contains water but that the water is isolated or otherwise prevented from solvating or reacting with the first component.

In another aspect of the invention is a solidifiable skin care or cleansing composition, including but not limited to:

a. a first component dispersed in a matrix capable of solidification at 25° C. (preferably where the moisture content of the solidified composition is less than about 20, 15, 10, 5, 3, 1 or 0.5% by wt.), the component being capable of chemically reacting with a second component that is different from the first component and which is optionally present in the matrix;

b. wherein the first component, the second component or both components are substantially unsolvated in said matrix (preferably where the solubility of either the first or second component in the matrix is less than about 5, 3, 2, 1, 0.5, or 0.1% by wt. at 25° C.); and c. wherein said matrix is water soluble or dispersible and contains at least one stabilizer selected from an organophilic particle, an amphipathic compound or polymer, or a crystalline hydroxyl containing stabilizer; and d. an anionic surfactant in a concentration of at least 2, 3, 57, 9, 10, 15, 20, or 30% by wt. when the at least one stabilizer consists solely of waxy particles, amphipathic compounds or polymers, or a combination thereof.

A solidifable composition is herein defined as a composition capable of being solidified by art recognized physical or chemical processes or any combination thereof.

In another aspect of the invention is a toilet bar, including but not limited to:
a. a solid base containing a soap, a non-soap anionic surfactant, or a combination thereof in a total concentration greater than about 10, 15, 20, 25, 30 or 40% by wt.;
b. a dispersed phase composed of a first component, the first component being capable of chemically reacting with a second component that is different from the first;
c. a continuous phase present in the composition composed of a substantially anhydrous carrier;
d. at least one stabilizer contained in the dispersed phase; wherein the first component is substantially unsolvated in the carrier;
e. wherein the dispersed and continuous phase separately form one or more domains of at least 1 mm average length along its major axis in the solid base; and
f. wherein the second component is contained in the solid base.

In a further aspect of the invention is a toilet bar, including but not limited to:
a. a solid base containing a soap, a non-soap anionic surfactant, or a combination thereof in a total concentration greater than about 10, 15, 20, 25, 30 or 40% by wt.;
b. a first dispersed phase composed of a first component, the first component being capable of chemically reacting with a second component that is different from the first;
c. a second dispersed phase containing the second component;
d. a first continuous phase present in the composition composed of a first substantially anhydrous carrier;
e. a second continuous phase present in the composition composed of a second substantially anhydrous carrier;
f. a stabilizer contained in each of the first and second dispersed phases; wherein the first component is substantially unsolvated in the first carrier and the second component is substantially unsolvated in the second carrier; and
g. wherein each of the first and second carriers form one or more separate domains of at least 1 mm average length along their major axis.

In another aspect of the invention is a method of treating the skin or hair, including but not limited to the steps of (carried out in any order):
a. contacting the skin or hair with a composition containing
  1. a dispersed phase composed of a first component capable of chemically reacting with a second component that is different from the first and which is optionally present in the dispersed phase;
  2. a continuous phase composed of a substantially anhydrous carrier (preferably where the moisture content of the carrier is less than about 1% by wt. preferably less than about 0.5% by wt. and more preferably where the carrier is immiscible in water);
  3. at least one stabilizer selected from an organophilic particle, an amphipathic compound or polymer, or a crystalline hydroxyl containing stabilizer;
  4 wherein the first component, the second component or both components are substantially unsolvated in the carrier (preferably where the reactive component's solubility in the carrier is less than about 5, 3, 2, 1, 0.5, or 0.1% by wt at 25° C.);
  5 an anionic surfactant in a concentration of at least 2, 3, 5, 7, 9, 10, 15, 20, or 30% by wt. when the at least one stabilizer consists solely of waxy particles, amphipathic compounds or polymers, or a combination thereof; and
b. adding water to the composition on the skin.

In another aspect of the invention is a method of treating the skin or hair, including but not limited the steps of (carried out in any order):
a. dispensing onto the skin or hair a solidifiable composition containing
  1. a first component dispersed in a matrix capable of solidification at 25° C. (preferably where the moisture content of the solidified composition is less than about 20, 15, 10, 5, 3, 1 or 0.5% by wt.), said component being capable of chemically reacting with a second component that is different from said first component and which is optionally present in the matrix;
  2. wherein the first component, the second component or both are substantially unsolvated in said matrix (preferably where the solubility of either the first or second component in the matrix is less than about 5, 3, 2, 1, 0.5, or 0.1% by wt. at 25° C.);
  3. wherein said matrix is water soluble or dispersible; and contains a stabilizer selected from an organophilic particle, an amphipathic compound or polymer, or a crystalline hydroxyl containing stabilizer;
  4. an anionic surfactant in a concentration of at least 2, 3, 5, 7, 9, 10, 15, 20, or 30% by wt. when the at least one stabilizer consists solely of waxy particles, amphipathic compounds or polymers, or a combination thereof; and
b. adding water to the solidified composition on the skin.

DETAILED DESCRIPTION OF THE INVENTION

In one aspect of the invention is a skin care or cleansing composition, including but not limited to:
a. a dispersed phase composed of a first component, the first component being capable of chemically reacting with a second component that is different from the first component
b. a continuous phase present in the composition composed of a substantially anhydrous carrier;
c. at least one stabilizer contained in the dispersed phase, wherein the stabilizer is selected from an organophilic particle, an amphipathic compound or polymer, or a crystalline hydroxyl containing stabilizer; and
d. wherein the first component is substantially unsolvated in the carrier (preferably where the reactive component's solubility in the carrier is less than about 5, 3, 2, 1, 0.5, or 0.1% by wt. at 25° C.); and
e. an anionic surfactant in a concentration of at least 2, 3, 5, 7, 9, 10, 15, 20, or 30% by wt. when the at least one stabilizer consists solely of waxy particles, amphipathic compounds or polymers, or a combination thereof.

In the inventive skin care or cleansing composition, the moisture content of the carrier is preferably less than about 5, 4, 3, 2, or 1% by wt., preferably less than about 0.9, 0.7, 0.5, 0.3, 0.1, 0.05, or 0.01% by wt. at 25 C.; more preferably the carrier is immiscible in water at 25 C. Advantageously the dispersed phase comprises the first and the second components and wherein the second component is substantially unsolvated in the carrier. Preferably the reaction of the first component with water or the first component and the second component is not polymerization.

Advantageously at least one reactive component has a particle size range of about 0.5 to 5000μ (preferably in the range of about 0.1 to 100μ, more preferably in the range of about 0.5 to 10μ). Preferably the stabilizer is substantially solvated in the continuous phase (preferably where the stabilizer solubility in the carrier is greater than about 1 gm/L at 25° C. preferably greater than about 5 gms/L at 25° C.). Preferably the stabilizer is an organophilic particle in the particle size range of about 0.02 to 250μ. In a preferred embodiment the stabilizer is selected from a waxy particle, organophilic silica, organophilic clay, or blends thereof. More preferably the stabilizer is an amphipathic compound or polymer with some oil soluble groups substantially solvated by the carrier and some polar groups substantially unsolvated by the carrier. In the case where the stabilizer is an amphipathic polymer it is preferably selected from polysiloxanes, polyalkylene ethers, polysaccharides, polyacrylates, or polystyrene each substituted with at least one linear or branched C8 to C24 alkyl or alkenyl chain.

Advantageously the carrier may contain components that are polar, nonpolar or a blend thereof. Preferably the first and second components do not substantially react with each other until dispersed or dissolved in water. Substantially react is herein defined as where no more than about 10, 5, 2, 1, 0.5 or 0.1% by wt. of the first component, the second component or both components reacts when stored at 50 C. for 60 days at 1 atm. In a preferred embodiment, the inventive composition further includes at least one dispersed surfactant that is substantially unsolvated by the carrier. In another preferred embodiment, the inventive composition includes structuring agents (e.g. fatty acids, fatty amides, trihyrdroxystearin and the like) that form lamellar, hexagonal, or cubic surfactant phases upon contact with water at 25 C.

Advantageously, the inventive composition has a first component that is capable of producing a gas in aqueous solution when reacted with an acid and the second component forms an acid in the presence of water. In another preferred embodiment, the first component is capable of generating a peroxide compound when dissolved in water. In a further preferred embodiment, the first component is capable of generating sulfide ions when reacted with an alkaline material and water.

Preferably the carrier contains an oil (preferably in a concentration range of about 10 to 100% by wt., preferably selected from triglyceride oils, mineral oils, silicones, blends thereof and the like); an emulsifier (preferably in a concentration range of about 2 to 35% by wt. and preferably selected from anionic, nonionic, amphoteric or cationic surfactants and blends thereof); preferably the stabilizer is an organophilic clay (preferably of the lipophilized, quaternary, or bentonite type or a blend thereof and the like, having a particle size range of about 0.2 to 250μ and is present in a concentration range of about 5 to 35% by wt.); and the composition contains a total of at least about 10% (or 5, 3, 1, 0.5, or 0.1%) of reactive dispersed solids by wt. (i.e. components that may chemically react with each other or with water, preferably selected from substantially anhydrous ammonium, amine, alkali and alkaline metal salts of carbonate, bicarbonate, organic, inorganic or organometallic acids, acid anhydrides or other acid precursors and blends thereof and the like). In a further embodiment, the first component is a solid or semisolid containing dissolved carbon dioxide.

In another aspect of the invention is a solidifiable skin care or cleansing composition, including but not limited to:
  a. a first component dispersed in a matrix capable of solidification at 25° C. (preferably where the moisture content of the solidified composition is less than about 20, 15, 10, 5, 3, 1 or 0.5% by wt.), the component being capable of chemically reacting with a second component that is different from the first component and which is optionally present in the matrix;
  b. wherein the first component, the second component or both components are substantially unsolvated in said matrix (preferably where the solubility of either the first or second component in the matrix is less than about 5, 3, 2, 1, 0.5, or 0.1% by wt. at 25° C.);
  c. wherein said matrix is water soluble or dispersible and contains at least one stabilizer selected from an organophilic particle, an amphipathic compound or polymer, or a crystalline hydroxyl containing stabilizer; and
  d. an anionic surfactant in a concentration of at least 2, 3, 5, 7, 9, 10, 15, 20, or 30% by wt. when the at least one stabilizer consists solely of waxy particles, amphipathic compounds or polymers, or a combination thereof.

Preferably the solidifiable skin care or cleansing composition is a solid matrix at 25 C; more preferably wherein the second component is substantially unsolvated in the matrix (preferably where the second component's solubility in the carrier is less than about 5, 3, 2, 1, 0.5, or 0.1% by wt. at 25° C.). More preferably the reaction of the first component with water or the first component and the second component is not polymerization. Advantageously the matrix may contain components that are polar, nonpolar or a blend thereof. Preferably the first and second components do not substantially react with each other until dispersed or dissolved in water.

In a further embodiment the matrix includes at least one surfactant that is substantially unsolvated by the matrix; and may further include structuring agents (e.g. fatty acids, fatty amides, trihydroxystearin and the like) that form lamellar, hexagonal, or cubic surfactant phases upon contact with water at 25 C.

In another embodiment is a composition wherein the first component is capable of producing a gas in aqueous solution when reacted with an acid and the second component forms an acid in the presence of water. Advantageously the composition contains a solidified oil or wax (preferably in a concentration range of about 10 to 100% by wt., preferably selected from triglyceride oil or waxes, mineral oils or waxes, silicones, and the like), and an emulsifier (preferably in a concentration range of about 2 to 35% by wt., preferably selected from anionic, nonionic, amphoteric or cationic surfactants and blends thereof).

Advantageously the composition contains a total of at least about 10% (or at least about 5, 3, 1, 0.5 or 0.1% by wt.) of one or more substantially anhydrous reactive materials selected from ammonium, amine, alkali and alkaline metal salts of carbonates, bicarbonates, organic acids, organic anhydrides, inorganic or organometalic acids, acid precursors and blends thereof). In a preferred embodiment the first component is a solid or semisolid containing dissolved carbon dioxide. In a further preferred embodiment, the first component is capable of generating sulfide ions when reacted with an alkaline material and water.

In another aspect of the invention is a toilet bar, including but not limited to:
  a. a solid base containing a soap, a non-soap anionic surfactant, or a combination thereof in a total concentration greater than about 10, 15, 20, 25, 30 or 40% by wt.;
  b. a dispersed phase composed of a first component, the first component being capable of chemically reacting with a second component that is different from the first;
  c. a continuous phase present in the composition composed of a substantially anhydrous carrier;

d. a stabilizer contained in the dispersed phase; wherein the first component is substantially unsolvated in the carrier;
e. wherein the dispersed and continuous phase separately form one or more domains of at least 1 mm average length along its major axis in the solid base; and
f. wherein the second component is contained in the solid base.

In a further aspect of the invention is a toilet bar, including but not limited to:
a. a solid base containing a soap, a non-soap anionic surfactant, or a combination thereof in a total concentration greater than about 10, 15, 20, 25, 30 or 40% by wt.;
b. a first dispersed phase composed of a first component, the first component being capable of chemically reacting with a second component that is different from the first;
c. a second dispersed phase containing the second component;
d. a first continuous phase present in the composition composed of a first substantially anhydrous carrier;
e. a second continuous phase present in the composition composed of a second substantially anhydrous carrier;
f. a stabilizer contained in each of the first and second dispersed phases; wherein the first component is substantially unsolvated in the first carrier and the second component is substantially unsolvated in the second carrier; and
g. wherein each of the first and second carriers form one or more separate domains of at least 1 mm average length along their major axis.

In another aspect of the invention is a method of treating the skin or hair, including but not limited to the steps (carried out in any order) of:
a. contacting the skin or hair with a composition containing
 1. a dispersed phase composed of a first component capable of chemically reacting with a second component that is different from the first and which is optionally present in the dispersed phase;
 2. a continuous phase composed of a substantially anhydrous carrier (preferably where the moisture content is less than about 1% by wt. preferably less than about 0.5% by wt. more preferably the carrier is immiscible in water);
 3. at least one stabilizer selected from an organophilic particle, an amphipathic compound or polymer, or a crystalline hydroxyl containing stabilizer; and
 4. wherein the first component, the second component or both components are substantially unsolvated in the carrier (preferably where the reactive component's solubility in the carrier is less than about 5, 3, 2, 1, 0.5, or 0.1% by wt. at 25° C.);
 5. an anionic surfactant in a concentration of at least 2, 3, 5, 7, 9, 10, 15, 20, or 30% by wt. when the at least one stabilizer consists solely of waxy particles, amphipathic compounds or polymers, or a combination thereof; and
b. adding water to the composition on the skin or hair.

Preferably the second component is the same as or is different from water. Advantageously the second component contains less than about 50, 40, 30, 20, 10, or 5% by wt. of water and where the second component is added to the first component before or after contacting the skin or hair with the first component.

In another aspect of the invention is a method of treating the skin or hair, including but not limited to the steps of (that can be carried out in any order):
a. contacting the skin or hair with a solidifiable composition containing
 1. a first component dispersed in a matrix capable of solidification at 25° C. (preferably where the moisture content of the solidified composition is less than about 20, 15, 10, 5, 3, 1 or 0.5% by wt.), said component being capable of chemically reacting with a second component that is different from said first component and which is optionally present in the matrix;
 2. wherein the first component, the second component or both are substantially unsolvated in said matrix (preferably where the solubility of either the first or second component in the matrix is less than about 5, 3, 2, 1, 0.5, or 0.1% by wt. at 25° C.);
 3. wherein said matrix is water soluble or dispersible and contains at least one stabilizer selected from an organophilic particle, an amphipathic compound or polymer, or a crystalline hydroxyl containing stabilizer;
 4. an anionic surfactant in a concentration of at least 2, 3, 5, 7, 9, 10, 15, 20, or 30% by wt. when the at least one stabilizer consists solely of waxy particles, amphipathic compounds or polymers, or a combination thereof; and
b. adding water to the solidified composition on the skin or hair.

Advantageously the composition is a solid at 25 C, and the second component is the same as or is different from water. Preferably the second component contains less than about 50, 40, 30, 20, 10, or 5% by wt. of water and the second component is added to the first component before or after contacting the skin or hair with the first component.

Reactive and Anhydrous Chemistry Configurations

Useful chemistry configurations include a cosmetic composition with suspended insolubilized surfactants in a solidified matrix or a substantially nonaqueous liquid carrier. Other useful chemistry systems may include effervescent cosmetic compositions, bleaching systems, or any system that may react with each other or with water and that are compatible with the other constituents of the inventive product.

Effervescent cosmetic compositions with particular ratios of different organic acids for different sensory effects which e.g. vary with water solubility such as citric, malic, tartaric, and fumaric acids combined with carbonate or bicarbonate salts where at least one of the acid or of the carbonate/bicarbonate salt is in the discontinuous phase may be used.

Bleaching systems may be used that contain anhydrous sodium perborate and/or sodium percarbonate and the like. These materials are hydrogen peroxide donors when in contact with water—preferably where the a pH is greater than about 7.0, 7.5, 8.0, 8.5, 9.0 or 9.5.

Depilatory systems may be used that contain a precursor acid that reacts with the base when the formulation is hydrated to form the active material for removing hair from the body. These acids may include such as thiolactic acid, thioglycolic acid and other aliphatic mercapto acids and the like. These materials may be activated by ingredient(s) within the dispersed phase (such as one or more alkaline materials or precursor(s) thereof), within the continuous phase, within both phases or by a component added to the inventive composition during product use such as water or encapsulated ingredient(s) liberated during product use such as by rubbing or by two packaging chambers which during use can be broken to allow for mixing of the two phases (such as water and the inventive composition).

Another preferred embodiment of the invention is a solid composition, such as a soap, a combo or syndet toilet bar which would contain regions of anyhdrous lotion. Blended within this anyhdrous lotion would be the reactive or interactive components—the components may be in separate domains or within the same domains. Once the bar is hydrated on the surface during the normal usage—the reactive or interactive ingredients would become solvated and become activated thus in one example altering and increasing the product lather, or in another example activating an active agent for the skin or hair, and the like.

Other useful additions to the inventive composition include materials with exothermic heats of solution or dispersion in water (such as zeolites and the like) or materials with endothermic heats of solution or dispersion in water (such as ammonium chloride, and the like). Carbon dioxide encapsulated by any suitable solid water soluble or dispersible material such as starch or sugar or blends thereof (such as Pop Rocks™, or chemicals that react to change color upon contact with water or with each other when solvated with water such as any water soluble or dispersible colorant e.g. blue 1, yellow 5 or 10, green 3, 5, or 7; blends thereof and the like.

The inventive cosmetic composition may also include reactive ingredients which are structured with waxes, polymers, etc. to form solid forms. The inventive cosmetic compositions may also contain an oil, an emulsifier, an organoclay, and 10% or more dispersed solids by weight, or may contain materials that impart a cooling sensation on the skin such as menthol and derivatives and the like.

Structurants and Stabilizers

Compositions according to the invention may also include in-use water structurants (such as lauric acid and trihydroxystearin); and stabilizers such as self-orienting/structuring organophilic particles which impart rheological elasticity (yield stress) such as organically modified clays (chemically reacted with fatty quaternium compounds for hydrophobicity) based on Hectorite, Bentonite, or synthetic clays such as Hydrotalcite that are available from Rheox/Elementis (Hightstown, N.J.), Southern Clay (Gonzales, Tex.), and SUD Chemie (Munich, Germany) respectively. Other useful components include elastomers such as those with silicone or nonsilicone backbones with different crosslinking groups, such as phenylated and polyvinyl crosslink linkages and the like. Specific useful elastomers include DC 9040 available from Dow Corning (Midland, Mich.), GE SFE818 available from General Electric (Waterford, N.Y.), Belsil RG 100 available from Wacker (Munich, Germany), and KSG 21 available from ShinEtsu (Tokyo, Japan). Such elastomers can act as stabilizers for the inventive composition.

Filler or oil absorbing particulates which are insoluble in the continuous phase may be advantageously used. Useful materials in this category include ultra-fine materials such as mica, talc, titanium dioxide, silica and starch. Finely powdered silicone polymers such as KSP 100 available from ShinEtsu may be used. Hollow and/or low density materials such as starch spheres (e.g. Natrasorb-W) available from National Starch (Bridgewater, N.J.), polymeric spheres (e.g. Expancel available from Akzo Nobel (Duluth, Ga.); and borosilicate glass spheres (e.g. Luxsil available from PQ corporation (Philadelphia, Pa.). These materials can act as stabilizers for the inventive composition.

Hydrophobic polymeric gellants may be used to adjust the viscosity of the continuous phase. Useful materials include Krayton Gel (e.g. Krayton D-1101 available from Krayton Polymers Corporation (Houston, Tex.); Hydrophobized PVP copolymers (e.g. Ganex series available from ISP Products Inc. (Wayne, N.J.); Silicone polymers (e.g. DC 2-1491) available from Dow Corning (Midland, Mich.), Acrylate polymers/copolymers (e.g.poly(sodium acrylate)) available from Rohm & Haas company (Philadelphia, Pa.); and Silicone-acrylate polymers (e.g. SA 70, VS 70, and VS80 available from 3M company (St. Paul, Minn.). These materials can also act as stabilizers for the inventive composition.

Crystalline hydroxyl-containing stabilizers including ethoxylated fatty alcohols (e.g. Neodol from Shell (Houston, Tex.) and trihydroxystearin (e.g. Thixcin-R from Rheox (Hightstown, N.J.) may be advantageously used.

Waxy materials such as organic waxes; silicone waxes. silicone-acrylate waxes, fatty amides may be useful in the inventive composition. Other useful components include high melt point hydrocarbons (e.g. having a melting point of greater than 55 C such as petrolatum. These materials can also act as stabilizers for the inventive composition.

Polymers that form water gels and travel to emulsion interfaces upon contact with water are also useful as stabilizers in the inventive composition such as Pemulen® (high molecular weight, cross linked copolymers of acrylic acid and a hydrophobic comonomer) and Carbopol® (high molecular weight homo- and copolymers of acrylic acid, optionally crosslinked with various substituents such as polyalkenyl polyethers) available from Noveon Chemicals (Cleveland, Ohio) and the like; Glyceril Polyacrylates (e.g. Lubrajel series from ISP (Wayne, N.J.)).

Surfactants

Soaps

The inventive product may contain a soap in its continuous or discontinuous phase. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. The soaps useful herein are the well known alkali metal salts of alkanoic or alkenoic acids having about 8 to 50 carbon atoms, preferably about 12 to about 22 carbon atoms. They may also be described as alkali metal carboxylates of alkyl or alkene hydrocarbons having about 12 to about 22 carbon atoms.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Anionic Surfactants

One or both of the continuous or discontinuous phases may also contain non-soap anionic surfactants. The anionic surfactant (which may comprise about 3 to 40% by wt. of both phases; 3 to 40% in the continuous phase and 3 to 40% in the discontinuous phase) may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate, and the like.

The anionic may also be an alkyl sulfate (e.g., $C_{12}$-$C_{18}$ alkyl sulfate) or alkyl ether sulfate (including alkyl glyceryl ether sulfates), and the like. Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates, and the like.

Sulfosuccinates may be monoalkyl sulfosuccinates having the formula:

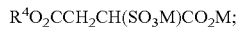
$R^4O_2CCH_2CH(SO_3M)CO_2M;$ amido-MEA sulfosuccinates of the formula

$R^4CONHCH_2CH_2O_2CCH_2CH(SO_3M)CO_2M$ wherein $R^4$ ranges from $C_8$-$C_{22}$ alkyl and M is a solubilizing cation;

amido-MIPA sulfosuccinates of formula

$RCONH(CH_2)CH(CH_3)(SO_3M)CO_2M$ where M is as defined above.

Also included are the alkoxylated citrate sulfosuccinates; and alkoxylated sulfosuccinates such as the following:

$$R\!-\!O\!-\!(CH_2CH_2O)_n\overset{\overset{O}{\|}}{C}CH_2CH(SO_3M)CO_2M$$

wherein n=1 to 20; and M is as defined above.

Sarcosinates are generally indicated by the formula RCON($CH_3$)$CH_2CO_2M$, wherein R ranges from $C_8$ to $C_{20}$ alkyl and M is a solubilizing cation.

Taurates are generally identified by formula

$R^2CONR^3CH_2CH_2SO_3M$ wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$R\!-\!(CH_2CH_2O)_nCO_2M$ wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in U.S. Pat. No. 5,393,466, Titled "Fatty Acid Esters Of Polyalkoxylated Isethionic Acid" issued Feb. 28, 1995 to Ilardi et al., hereby incorporated by reference into the subject application. This compound has the general formula:

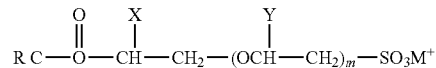

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Zwitterionic and Amphoteric Surfactants

One or both of the continuous or discontinuous phases may also contain zwitterionic/amphoteric surfactants. Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

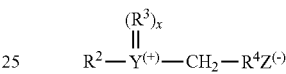

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

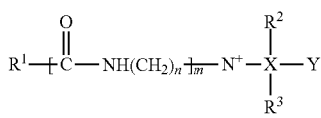

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

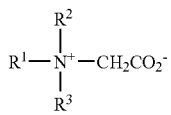

and amido betaines of formula:

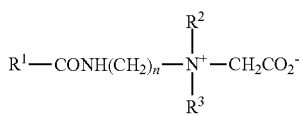

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl. A suitable betaine is cocoamidopropyl betaine.

A further possibility is that the amphoteric detergent is a sulphobetaine of formula

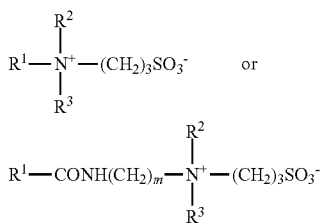

where m is 2 or 3, or variants of these in which —$(CH_2)_3SO^-_3$ is replaced by

In these formulae $R^1$, $R^2$ and $R^3$ are as discussed previously.

Amphoacetates and diamphoacetates are also intended to be covered in possible zwitterionic and/or amphoteric compounds which may be used, especially C8-C20 amphoacetates or mixtures thereof, and the like. A suitable amphoacetate is sodium laurylamphoacetate.

The amphoteric/zwitterionic surfactant, when used, generally comprises about 2 to 30%, preferably about 3 to 20% by weight, more preferably about 3 to 10% of the composition. 2 to 30% in the continuous phase and 1 to 5% in the discontinuous phase).

A preferred surfactant system of the invention comprises the following: anionic surfactant (e.g. alkali metal alkyl ethersulfate), about 2-50%; amphoteric surfactant (e.g. alkyl betaine or alkyl amphoacetate), about 3-20% based on the total composition.

The surfactant system may also optionally comprise a nonionic surfactant. The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides, and the like.

The nonionic may also be a sugar amide, such as a polysaccharide amide. Specifically, the surfactant may be one of the lactobionamides described in U.S. Pat. No. 5,389,279 titled "Compositions comprising nonionic glycolipid surfactants" issued on Feb. 14, 1995 to Au et al. which is hereby incorporated by reference or it may be one of the sugar amides described in U.S. Pat. No. 5,009,814 titled "Use of n-polyhydroxyalkyl fatty acid amides as thickening agents for liquid aqueous surfactant systems" issued on Apr. 23, 1991 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 titled "Foaming surfactant compositions", issued on Jan. 21, 1986 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The nonionic comprises about 0 to 40% by wt. in each phase of the composition, preferably about 0 to 15% by wt. 0 to 40% in the continuous phase and 0 to 20% in the discontinuous phase).

Occlusive Emollients

One way of moisturizing is to reduce the rate of water loss from the stratum corneum (skin surface) by depositing an occlusive emollient on the skin surface which prevents water evaporation. Another technique is to add hygroscopic nonocclusive substances (humectants), which will retain water to the stratum corneum, making water available to the skin surface thereby producing the desired cosmetic effect. Nonocclusive emollients also function by improving the lubricity of the skin. Both occlusive and nonocclusive emollients as well as mixtures thereof are operative in the present invention and may be present in either or both the continuous or discontinuous phases. Examples of occlusive emollients include, lanolin and its derivatives, long chain esters, waxes, saturated and unsaturated fatty alcohols, conditioning oils and extracts, phospholipids, sterols, ceramides and silicones. The following occlusive emollients may optionally be found in the compositions of the invention.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and the like.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and the like.

Animal Fats: acetylated lanolin alcohols, lanolin, lard, mink oil and tallow, and the like.

Other examples of occlusive emollients include mineral oil, petrolatum, silicone oil such as dimethyl polysiloxane, lauryl and myristyl lactate, fatty acid oils, triglycerides, and the like.

The occlusive emollient is generally used in an amount from about 0 to 70%, preferably about 5 to 40% by wt. of the phase in which it is found in. Generally, it should comprise no more than 70% of such phase. A portion of the emollient may be present in the form of solid or semi-solid beads. The beads are optionally used in an amount from about 0.01, 0.05, 0.1, 0.5 or 1.0% by wt. to about 5, 10, 15 or 20% by wt.

Nonocclusive Emollients

Some examples of nonocclusive emollients are liquid water-soluble polyols, glycerin, propylene glycol, sorbitol, polyethylene glycol, ethoxylated/propoxylated ethers of methyl glucose (eg., methyl gluceth-20) and ethoxylated/propoxylated ethers of lanolin alcohol e.g., Solulan-75). Some other preferred moisturizers are the nonoclusive liquid water soluble polyols and the essential amino acid compounds found naturally in the skin. Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA. Other examples of both types occlusive and nonocclusive emollients are disclosed in "Emollients—a Critical Evaluation," by J. Mausner Cosmetics & Toiletries, May 1981, incorporated herein by reference.

In addition, the continuous or discontinuous phases of the compositions of the invention may include optional ingredients as follows:

Sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300), quaternary ammonium compounds; preservatives such as dimethyloldimethylhydantoin (Glydant XL1000), parabens, sorbic acid etc.

The compositions may also comprise coconut acyl mono- or diethanol amides and the like as suds boosters.

Antioxidants such as, for example, butylated hydroxytoluene (BHT) may be used advantageously in amounts of about 0.01% or higher if appropriate.

Cationic conditioners which may be used include Polyquaternium-10, Quatrisoft LM-200, Polyquaternium-24, Merquat Plus 3330, Polyquaternium 39, Ucare polymer JR400, Jaguar® type conditioners and the like.

Another optional ingredient which may be added are the deflocculating polymers such as are taught in U.S. Pat. No. 5,147,576 titled "Liquid Detergent Composition In The Form Of Lamellar Droplets Containing A Deflocculating Polymer", issued on Sep. 15, 1992 to Montague, hereby incorporated by reference.

Other ingredients which may be included are exfoliants such as polyoxyethylene beads, silica particles, walnut shells and apricot seeds, and the like. pH and viscosity adjusters may be optionally used to e.g. adjust the pH of the separate phases prior to being combined into the inventive product. Such suitable pH adjusters may include citric acid, glycolic acid, lactic acid, other alpha or beta hydroxy acids, and the like.

The invention will now be described in greater detail by way of the following non-limiting examples. The examples are for illustrative purposes only and not intended to limit the invention in any way.

Except in the examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLE 1

An inventive cleansing composition having a hydrophilic continuous phase may be prepared according to table 1. A combination of anionic and amphoteric surfactants were added to each phase. The composition is useful as a shampoo and for oily skin cleansing.

TABLE 1

| Component | Concentration (w/w) |
|---|---|
| Water Soluble Anhydrous Fluid [1] | 25% |
| Non Polar Oil [2] | 5% |
| Ethoxylated Fatty Alcohol | 5% |
| Emollient Ester | 4% |
| Fatty Amide | 1% |
| Hydrocarbon/Silicone Wax [3] | 2% |
| Glyceryl Polyacrylate | 10% |
| Anhydrous Suspended or Solubilzed Anionic Surfactant Powder | 12% |
| Anhydrous Suspended or Solubilized Amphoteric Surfactant Powder | 2% |
| Hydrophilic Structuring Polymer [4] | 2% |
| Sodium Bicarbonate | 15% |
| Citric Acid | 15% |
| Fragrance | 2% |
| TOTAL | 100% |

[1] such as propylene glycol or glycerine
[2] such as polyisobutene
[3] such as paraffin or ShinEtsu KP 100 Silicone acrylate wax
[4] such as pemulen or carbopol

EXAMPLE 2

An inventive lotion composition may be prepared according to table 2.

TABLE 2

| Components | Concentration (w/w) |
|---|---|
| Non-Polar Oil | 30% |
| Ethoxylated Fatty Alcohol | 5% |
| Emollient Ester [5] | 5% |
| Fatty Amide [6] | 2% |
| Organic/Silicone Wax | 3% |
| Liquid Emulsifier [7] | 5% |
| Suspended water gellant [8] | 2% |
| Organic modified clay [9] | 10% |
| Hydrophobic Polymeric Structurant [10] | 3% |
| Sodium Bicarbonate | 15% |
| Citric Acid | 15% |
| Fragrance | 5% |
| TOTAL | 100% |

[5] such as isopropyl myristate
[6] such as glyceryl stearamide
[7] such as Brij 93 Veg from Unichema
[8] such as pemulen or carbopol
[9] such as Bentone 38 V from Rheox
[10] such as Krayton gel

EXAMPLE 3

An inventive moisturizing cleansing composition having color changing properties when blended with water may be prepared according to the composition in table 3.

TABLE 3

| Components | Concentration (w/w) |
|---|---|
| Sunflower Seed Oil | 27.99% |
| Neodol 45 (ethoxylated fatty alcohol) | 10% |
| Bentone 38 ISD GEL (Organoclay) | 15% |
| Tauranol I78 (Sodium Cococoyl Isethionate Powder) | 10% |
| Brij 93 Vej | 5% |
| Sodium Bicarbonate | 15% |
| Citric Acid | 15% |
| Green #3 | 0.01% |
| Fragrance | 2% |
| TOTAL | 100% |

EXAMPLE 4

An inventive wash-off moisturizing composition may be prepared according to table 4.

TABLE 4

| Components | Concentration (w/w) |
|---|---|
| Sunflower Seed Oil | 45% |
| Bentone 38 ISD GEL (Organoclay) | 15% |
| Tauranol I78 (Sodium Cocoyl Isethionate Powder) | 1% |
| Brij 93 Vej | 9% |
| Sodium Bicarbonate | 12.5% |
| Citric Acid | 12.5% |
| Fragrance | 5% |
| TOTAL | 100% |

EXAMPLE 5

An inventive moisturizing cleansing and conditioning composition may be prepared according to table 5.

TABLE 5

| Components | Concentration (w/w) |
|---|---|
| Non-Polar Oil | 20% |
| Fatty Alcohol | 4% |
| Ethoxylated Fatty Alcohol | 6% |
| Emolient Ester | 5% |
| Fatty Amide | 2% |
| Organic/Silicone Wax | 3% |
| Anhydrous Suspended Anionic Surfactant Powder | 8% |
| Anhydrous Suspended Amphoteric Surfactant Powder | 2% |
| Organic Clay | 15% |
| Hydrophobic Polymeric Structurant | 3% |
| Sodium Bicarbonate | 15% |
| Citric Acid | 15% |
| Fragrance | 2% |
| TOTAL | 100% |

EXAMPLE 6

An inventive lotion composition may be prepared according to table 6.

TABLE 6

| Components | Concentration (w/w) |
|---|---|
| Sunflower Seed Oil | 45% |
| Bentone 38 ISD GEL (Organoclay) | 15% |

TABLE 6-continued

| Components | Concentration (w/w) |
|---|---|
| Brij 93 Vej | 5% |
| Sodium Bicarbonate | 15% |
| Citric Acid | 15% |
| Fragrance | 5% |
| TOTAL | 100% |

EXAMPLE 7

An inventive water-activated hair bleaching composition may be prepared according to table 7.

TABLE 7

| Components | Concentration (w/w) |
|---|---|
| Sunflower Seed Oil | 35% |
| Bentone 38 ISD GEL (Organoclay) | 15% |
| Brij 93 Vej | 5% |
| Neodol 45 (Ethoxylated Fatty Alcohol) | 20% |
| Sodium Perborate | 15% |
| Sodium Carbonate | 5% |
| Fragrance | 5% |
| TOTAL | 100% |

EXAMPLE 8

An inventive solid water-activated cleansing and conditioning composition may be prepared according to table 8.

TABLE 8

| Components | Concentration (w/w) |
|---|---|
| Non-Polar Oil | 10% |
| Fatty Alcohol | 4% |
| Ethoxylated Fatty Alcohol | 6% |
| Emolient Ester | 5% |
| Organic/Silicone Wax | 25% |
| Anhydrous Suspended Anionic Surfactant Powder | 8% |
| Anhydrous Suspended Amphoteric Surfactant Powder | 2% |
| Organic Clay | 15% |
| Hydrophobic Polymeric Structurant | 3% |
| Sodium Bicarbonate | 10% |
| Citric Acid | 10% |
| Fragrance | 2% |
| TOTAL | 100% |

EXAMPLE 9

An inventive water-activated depilatory composition may be prepared according to table 9.

TABLE 9

| Components | Concentration (w/w) |
|---|---|
| Sunflower Seed Oil | 29.5% |
| Bentone 38 ISD GEL (Organoclay) | 15% |
| Brij 93 Vej | 5% |

TABLE 9-continued

| Components | Concentration (w/w) |
|---|---|
| Neodol 45 (Ethoxylated Fatty Alcohol) | 20% |
| Thiolactic Acid (Powder) | 13% |
| Sodium Bicarbonate | 5% |
| Calcium Hydroxide (Fine Powder) | 12%* |
| Fragrance | 0.5% |
| TOTAL | 100% |

*Calcium Hydroxide is used at a level sufficient to provide a pH of 10.5 to 12.5 in a saturated aqueous solution of the depilatory composition.

EXAMPLE 10

An inventive composition in the form of a toilet bar may be prepared according to tables 10 and 10(b). The inventive bar contains a dehydrated (i.e. rehydratable) cream having a domain size of at least 1 mm along the domain's major axis, where one or more reactive materials are found in the cream portion, and a second reactive material is contained in the bar soap base itself. In the presence of water during lathering, these materials will react and create a benefit for the skin. The effervescence caused by the reaction should provide an enhanced lather volume which would otherwise be depressed by the cream.

The soap base can be of varying ratios of the different fatty acid soap components. The minor components can be the common ingredients used in soap bar manufacture including emollients, antibacterial agents, colorants, opacifiers, brighteners etc. The mixed mass is then milled/refined and plodded. The plodded bars are pressed into the desired shape.

TABLE 10

| Components of Rehydratable Cream | Wt % in cream | Wt % in Bar @ 15% dose of cream in bar |
|---|---|---|
| Stearic acid | 23 | 3.5 |
| Glycerol monostearate | 18 | 2.7 |
| Cetyl alcohol | 14.5 | 2.2 |
| Triethanolamine | 5.3 to 9.8 | 0.8 to 1.5 |
| Petrolatum | 7 | 1.1 |
| Ceresin wax | 12.9 to 38.7 | 1.9 to 5.8 |
| Nonionic surfactants (emulsifiers) | | |
| Laureth 23/Brij 35 | 3.7 | 0.55 |
| Anionic surfactants | | |
| Alpha Olefin Sulfonate | 0 to 9 | 0 to 1.35 |
| Sodium Lauryl Sulfate | 0 to 9 | 0 to 1.35 |
| Sodium Lauryl Ether Sulfate | 0 to 4 | 0 to 0.63 |
| Citric Acid | 10 to 25 | 1.5 to 3.75 |
| Mica | 0 to 2 | 0 to 0.3 |
| Water | 0 to 5 | 0 to 0.75 |

TABLE 10(b)

| Material | Wt % of Bar Soap Tallow/ Coco base | Wt % of Bar Soap Combo bar base | Wt % of Bar Soap Syndet Bar base |
|---|---|---|---|
| Soap Base(1) | 60-80 | 50-70 | 5-15 |
| Water | 4.0-15 | 6-15 | 4.0-8.0 |
| Co-Surfactants (sodium cocoylisethionate, etc) | 0 | 20-40 | 30-55 |
| Preservatives | 0.03-0.05 | 0.03-0.05 | 0.03-0.05 |
| Fragrance | 1 | 1 | 1 |
| Colorant | 0.1-0.5 | 0.1-0.5 | 0.1-0.5 |

TABLE 10(b)-continued

| Material | Wt % of Bar Soap Tallow/ Coco base | Wt % of Bar Soap Combo bar base | Wt % of Bar Soap Syndet Bar base |
|---|---|---|---|
| Total Rehydratable Cream(s) | 15-40 | 10-20 | 10-20 |
| Total vegetable, petroleum or silicone oil(s) | 6.0-10.0 | 6.0-10.0 | 6.0-10.0 |
| Sodium Bicarbonate | 5-20 | 5-20 | 5-20 |
| Total | 100 | 100 | 100 |

EXAMPLE 11

An inventive composition in the form of a toilet bar may be prepared according to tables 11(a) and (b). The inventive bar contains dehydrated cream, having a domain size of at least 1 mm along its major axis, where one or more reactive materials are found in the first cream portion, and a second reactive material is contained in a second cream portion both are mixed into the bar soap base itself. The two phases may be mixed in a chip mixer together then milled or refined then plodded into billets which can be stamped. It may also be possible to maintain the 2 phases separate in the milling or refining process and coextrude the 2 phases prior to stamping the bars.

In the presence of water during lathering, these materials will react and create a benefit, i.e. the effervescence caused by the reaction should provide an enhanced lather volume which would otherwise be depressed by the cream.

TABLE 11a

| Components of Rehydratable Cream | Wt % in cream 1 | Wt % in cream 2 | Wt % in Bar @7.5% dose of cream 1 and 7.5% cream 2 respectively |
|---|---|---|---|
| Stearic acid | 23 | 23 | 3.5 |
| Glycerol monostearate | 18 | 18 | 2.7 |
| Cetyl alcohol | 14.5 | 14.5 | 2.2 |
| Triethanolamine | 5.3 to 9.8 | 5.3 to 9.8 | 0.8 to 1.5 |
| Petrolatum | 7 | 7 | 1.1 |
| Ceresin wax | 12.9 to 38.7 | 12.9 to 38.7 | 1.9 to 5.8 |
| Nonionic surfactants (emulsifier) | | | |
| Laureth 23/Brij 35 | 3.7 | 3.7 | 0.55 |
| Anionic surfactants | | | |
| Alpha Olefin Sulfonate | 0 to 9 | 0 to 9 | 0 to 1.35 |
| Sodium Lauryl Sulfate | 0 to 9 | 0 to 9 | 0 to 1.35 |
| Sodium Lauryl Ether Sulfate (2 or 3 eo). | 0 to 4 | 0 to 4 | 0 to 0.63 |
| Citric Acid | 10 to 25 | 0 | 1.5 to 3.75 |
| Sodium Bicarbonate | 0 | 10 to 25 | 1.5 to 3.75 |
| Mica | 0 to 2 | 0 to 2 | 0 to 0.3 |
| Water | 0 to 5 | 0 to 5 | 0 to 0.75 |

TABLE 11(b)

| Material | Wt % of Bar Soap Tallow/ Coco base | Wt % of Bar Soap Combo bar base | Wt % of Bar Soap Syndet Bar base |
|---|---|---|---|
| Soap Base(1) | 60-80 | 50-70 | 5-15 |
| Water | 4.0-15 | 6-15 | 4.0-8.0 |
| Co-Surfactants (sodium cocoylisethionate, etc) | 0 | 20-40 | 30-55 |
| Preservatives | 0.03-0.05 | 0.03-0.05 | 0.03-0.05 |
| Fragrance | 1 | 1 | 1 |
| Colorant | 0.1-0.5 | 0.1-0.5 | 0.1-0.5 |
| Rehydratable Creams 1 and 2 | 15-40 | 10-20 | 10-20 |
| Total vegetable, petroleum or silicone oil(s) | 6.0-10.0 | 6.0-10.0 | 6.0-10.0 |
| Total | 100 | 100 | 100 |

(1)The soap base can be of varying ratios of the different fatty acid soap components.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A liquid or flowable skin care or cleansing composition for treating the skin or hair, comprising:
    (a) a dispersed phase including a first component, and a second component that is different from the first, the first component being capable of chemically reacting with the second component;
    (b) a continuous phase present in the composition composed of a substantially anhydrous carrier; wherein the carrier contains an occlusive skin emollient oil comprising triglyceride oils, mineral oils, silicones or blends thereof in a concentration range of about 10 to 100% by wt.;
    (c) an organophilic particle stabilizer contained in the dispersed phase;
    (d) wherein the first component is substantially unsolvated in the carrier;
    (e) an anionic surfactant in a concentration of at least 2% by wt. when the organophilic particle stabilizer consists solely of waxy particles;

(f) wherein neither the first nor the second components is encapsulated in a barrier material and do not substantially react with water or each other until dispersed or dissolved in water during cleansing or skin treatment by user; and (g) wherein the skin care or cleansing composition is liquid or flowable at 25° C.;

wherein capability of the first component to react with the second component comprises the following embodiments:

i. the first component is capable of producing a gas in aqueous solution when reacted with an acid and second component is an acid or forms an acid in the presence of water;

ii. the first component is capable of generating a peroxide compound when dissolved in water; and iii. the first component is capable of generating sulfide ions when reacted with an alkaline material and water.

2. The composition of claim 1 wherein the reaction of the first component with the second component is not polymerization.

3. The composition of claim 1 wherein the at least one reactive component has a particle size range of about 0.5 to 5000 μm.

4. The composition of claim 1 wherein the organophilic particle stabilizer is in the particle size range of about 0.02 to 250 μm.

5. The composition of claim 4 wherein the organophilic particle stabilizer is a waxy particle, organophilic silica, organophilic clay, or blends thereof.

6. The composition of claim 1 further comprising dispersed surfactants that are substantially unsolvated by the carrier.

7. The composition of claim 1 further comprising structuring agents that form lamellar, hexagonal, or cubic surfactant phases upon contact with water at 25° C.

8. The composition of claim 1 wherein the carrier contains an oil, an emulsifier and wherein the organophilic particle stabilizer is an organophilic clay; and the composition contains a total of at least about 10% of reactive dispersed solids by wt.

9. A method of treating the skin or hair, comprising the steps of:

(a) contacting the skin or hair with a composition containing (1) a dispersed phase composed of a first component capable of chemically reacting with a second component that is different from the first and which is present in the dispersed phase;

(2) a continuous phase composed of a substantially anhydrous carrier; wherein the carrier contains an occlusive skin emollient oil comprising triglyceride oils, mineral oils, silicones or blends thereof in a concentration range of about 10 to 100% by wt.;

(3) an organophilic particle stabilizer contained in the dispersed phase;

(4) wherein the first component is substantially unsolvated in the carrier;

(5) an anionic surfactant in a concentration of at least 2% by wt. when the at least one stabilizer consists solely of waxy particles;

(6) wherein neither the first nor the second component is encapsulated in a barrier material and do not substantially react with water or each other until dispersed or dissolved in water during cleansing or skin treatment by user;

(7) wherein the skin care or cleansing composition is liquid or flowable at 25° C.; and wherein capability of the first component to react with the second component comprises the following embodiments:

i. the first component is capable of producing a gas in aqueous solution when reacted with an acid and second component is an acid or forms an acid in the presence of water;

ii. the first component is capable of generating a peroxide compound when dissolved in water; and iii. the first component is capable of generating sulfide ions when reacted with an alkaline material and water, (b) adding water to the composition on the skin or hair.

10. The method of claim 9 where the second component is the same as or is different from water.

* * * * *